(12) United States Patent
Blacker

(10) Patent No.: US 12,396,741 B2
(45) Date of Patent: Aug. 26, 2025

(54) SYSTEMS AND METHODS FOR THROMBUS ASPIRATION

(71) Applicant: Corindus, Inc., Newton, MA (US)

(72) Inventor: Steven J. Blacker, Framingham, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 464 days.

(21) Appl. No.: 17/930,430

(22) Filed: Sep. 8, 2022

(65) Prior Publication Data

US 2024/0081844 A1 Mar. 14, 2024

(51) Int. Cl.
*A61B 17/22* (2006.01)
*A61B 17/00* (2006.01)
*A61B 90/00* (2016.01)

(52) U.S. Cl.
CPC .... *A61B 17/22* (2013.01); *A61B 2017/00022* (2013.01); *A61B 2017/00212* (2013.01); *A61B 2017/22079* (2013.01); *A61B 2090/064* (2016.02)

(58) Field of Classification Search
CPC .......... A61B 17/12; A61B 2017/22079; A61B 2017/00022; A61B 2017/00212; A61B 2017/00115; A61B 5/14514; A61B 5/150099; A61B 5/0055; A61B 5/150053; A61B 5/150145; A61B 2217/005; A61B 2090/064; A61B 17/22; A61M 1/0209; A61M 1/0236; A61M 1/73; A61M 1/74; A61M 1/90
See application file for complete search history.

(56) References Cited

U.S. PATENT DOCUMENTS

| | | | |
|---|---|---|---|
| 9,248,221 B2 * | 2/2016 | Look | A61M 1/84 |
| 2017/0100142 A1 | 4/2017 | Look et al. | |
| 2018/0326181 A1 * | 11/2018 | Kokish | A61B 34/30 |
| 2019/0105113 A1 | 4/2019 | Popovic et al. | |
| 2021/0298772 A1 * | 9/2021 | Kaethner | A61B 34/20 |
| 2022/0008090 A1 * | 1/2022 | Look | A61M 1/74 |
| 2022/0168001 A1 * | 6/2022 | Naglretter | A61B 17/22 |

FOREIGN PATENT DOCUMENTS

| | | | |
|---|---|---|---|
| CN | 113413191 | 9/2021 | |
| CN | 113413191 A * | 9/2021 | ............. A61B 17/22 |
| JP | 2021534851 | 12/2021 | |

(Continued)

OTHER PUBLICATIONS

European Search Report for Corresponding EP Application No. 23196076, dated Feb. 2, 2024.

*Primary Examiner* — Todd J Scherbel

(57) ABSTRACT

Systems and methods include positioning of a catheter lumen in a first position with respect to a thrombus, the catheter lumen defined by a catheter, initiating of evacuation of a tubing lumen, where the tubing lumen is not in fluid communication with the catheter lumen, determination that a pressure within the tubing lumen is equal to or less than a target aspiration pressure, and, in response to the determination that the pressure within the tubing lumen is equal to or less than a target aspiration pressure, automatic establishment of fluid communication between the tubing lumen and the catheter lumen.

12 Claims, 13 Drawing Sheets

(56) References Cited

FOREIGN PATENT DOCUMENTS

| JP | 2021534851 | A | * | 12/2021 | ............... | A61F 2/01 |
| WO | 2017062927 | A2 | | 4/2017 | | |
| WO | 2018136931 | | | 7/2018 | | |
| WO | 2020023541 | | | 1/2020 | | |
| WO | WO-2020023541 | A1 | * | 1/2020 | ............. | A61B 17/22 |
| WO | 2022154979 | | | 7/2022 | | |

* cited by examiner

SYSTEMS AND METHODS FOR THROMBUS ASPIRATION

BACKGROUND

As used herein, the term elongated medical device (EMD) refers to, but is not limited to, catheters (e.g., guide catheters, microcatheters, aspiration catheters, balloon/stent catheters), wire-based devices (e.g., guidewires, microwires, embolization coils, stent retrievers, etc.), and medical devices comprising any combination of the above. Generally, EMDs may be used for many minimally-invasive medical procedures. Such procedures may facilitate the diagnosis and treatment of diseases of various vascular systems, and include neurovascular interventional (NVI) (or neurointerventional) surgery, percutaneous coronary intervention (PCI), and peripheral vascular intervention (PVI). Generally, these procedures involve navigating a guidewire through patient vasculature, and advancing a working catheter via the guidewire to deliver therapy.

A catheterization procedure starts by gaining access into an appropriate vessel, such as an artery or vein, by inserting a sheath therein. Next, for example, a diagnostic guidewire is advanced within the sheath to a primary location such as an internal carotid artery (in NVI), a coronary ostium (in PCI) or a superficial femoral artery (in PVI). A guide catheter is then advanced over the diagnostic guidewire to the primary location. The diagnostic guidewire is removed, and a guidewire suitable for navigating the target vasculature is then pushed through the guide catheter to a target location (e.g., lesion, thrombus) within the vasculature. In certain situations, such as in the case of tortuous anatomy, a support catheter or microcatheter is inserted over the guidewire to assist in navigating the guidewire therethrough.

In order to navigate the guidewire or guidewire/microcatheter toward the target location, a physician advances the guidewire or guidewire/microcatheter while manipulating its proximal end so as to direct the distal tip into appropriate vessel branches along the path to the target location, while avoiding advancing into other vessel branches. Prior to the procedure, the physician may use an imaging system (e.g., a fluoroscope) to obtain successive contrast-enhanced images of the patient vasculature and may select one of the images for use as a roadmap to navigate the guidewire or guidewire/microcatheter to the target location. Contrast-enhanced images are also obtained while the physician navigates the guidewire or guidewire/microcatheter so that the physician can verify that the device is moving along the correct path to the target location.

Robotic catheter-based procedure systems facilitate the above processes by supporting each of the guidewires and catheters and physically manipulating each of the guidewires and catheters as desired by a physician. For example, a robotic catheter-based procedure system may hold a guidewire and include mechanical components to advance, retract and rotate the guidewire in response to physician commands. The physician may provide such commands via input devices (e.g., joysticks, buttons, scroll wheels, touch screens) mounted to a control console. The input devices may allow the physician to select one or more guidewires and/or catheters to be controlled at a given time. Robotic catheter-based procedure systems may thereby provide greater control and accuracy than purely manual catheterization procedures. Moreover, the control console and thus the physician may be shielded from x-rays emitted by the imaging system used to track the locations of the guidewires and/or catheters during the procedures.

Robotic catheter-based procedure systems may be used to assist a physician in performing catheterization procedures such as, for example, NVI, PCI and PVI. Examples of robotic-assisted NVI procedures include coil embolization of aneurysms, liquid embolization of arteriovenous malformations and mechanical thrombectomy of large vessel occlusions in the case of acute ischemic stroke. In such NVI procedures, a physician uses a robotic system to gain lesion access by manipulating a neurovascular guidewire and microcatheter to deliver therapy which restores normal blood flow. Access is provided using a sheath or guide catheter as described above but may also require an intermediate catheter to provide additional distal territory and/or to provide adequate support for the microcatheter and guidewire. The distal tip of a guidewire is navigated into or past the lesion depending on the type of lesion and treatment. For treating aneurysms, the microcatheter is advanced into the lesion, the guidewire is removed, and several coils are deployed into the aneurysm through the microcatheter. The coils are then used to embolize the aneurysm. For treating arteriovenous malformations, a liquid embolic is injected into the malformation via the microcatheter.

In conventional mechanical thrombectomy, aspiration may be used to treat vessel occlusions. Aspiration may be performed directly through the aforementioned microcatheter or using a larger-bore aspiration catheter. Once the microcatheter or aspiration catheter has been navigated to the occluding thrombus, an aspiration pump connected thereto is activated to generate negative pressure which causes the thrombus to be pulled into the catheter. Conventional aspiration systems may require significant time to completely remove a thrombus from a vessel. Additionally, conventional systems may generate and apply the negative pressure longer than is required to remove the thrombus. Either of these shortcomings increases risk of injury to the vasculature and/or to the aspiration pump. Systems are desired to improve the efficiency, efficacy and/or safety of mechanical thrombectomy using robotic catheter-based procedure systems.

DETAILED DESCRIPTION

Figure 1:
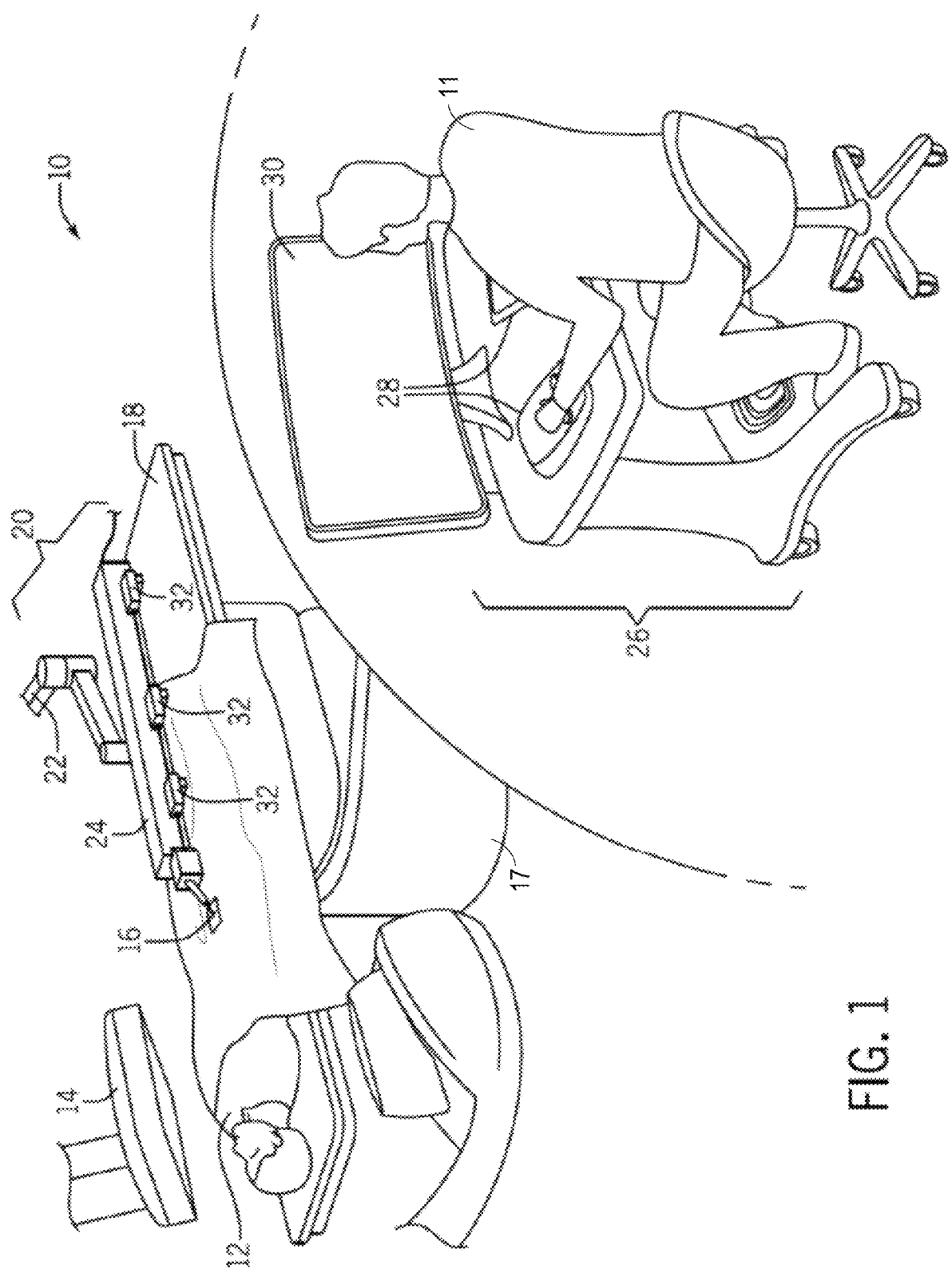
FIG. 1 is a perspective view of a robotic catheter-based procedure system in accordance with some embodiments.

The following description is provided to enable any person in the art to make and use the described embodiments. Various modifications will remain apparent to those in the art.

According to some embodiments, aspiration of a thrombus is initiated only after a determination that an aspiration (i.e., vacuum) source has reached a threshold negative pressure. Such initiation increases removal effectiveness, resulting in faster removal of the thrombus in many instances.

In one example, an aspiration catheter lumen defined by an aspiration catheter is positioned in a first position with respect to a thrombus. Evacuation is then initiated of a tubing lumen which is not in fluid communication with the aspiration catheter lumen. After a period of time, it is determined that a pressure within the tubing lumen is equal to or less than a target aspiration pressure. In response to the determination that the pressure within the tubing lumen is equal to or less than a target aspiration pressure, fluid communication is automatically established (e.g., by opening a valve, by releasing a clamp) between the tubing lumen and the aspiration catheter lumen. Such a process may serve to evacuate the thrombus more quickly than otherwise. In some aspects, an operator is informed that the pressure within the tubing lumen is equal to or less than the target aspiration pressure, and the operator transmits a command to automatically establish fluid communication between the tubing lumen and the aspiration catheter lumen.

Embodiments may further determine whether the pressure within the tubing lumen is greater than a second pressure and, if it is determined that the pressure within the tubing lumen is greater than the second pressure, automatically terminate (e.g., by closing a valve, by engaging a clamp) fluid communication between the tubing lumen and the aspiration catheter lumen. These aspects may minimize aspiration time to that which is actually needed to remove the thrombus.

Similarly, some aspects include presentation of an indication to an operator that the pressure within the tubing lumen is greater than the second pressure. After presenting the indication, and while the pressure within the tubing lumen is greater than the second pressure, fluid communication between the tubing lumen and the aspiration catheter lumen is automatically terminated in response to receipt of a command from the operator.

Embodiments may also include repositioning the aspiration catheter as necessary during the procedure to maintain a suitable position of the tip of the aspiration catheter relative to the face of the thrombus. For example, after automatically establishing fluid communication between the tubing lumen and the aspiration catheter, and before determining whether the pressure within the tubing lumen is greater than a second pressure, it is determined whether the pressure within the tubing lumen is within a predefined range. If it is determined that the pressure within the tubing lumen is within the predefined range, the position of the aspiration catheter lumen is automatically adjusted until the pressure within the tubing lumen is less than a threshold aspiration pressure.

FIG. 1 is a perspective view of catheter-based procedure system 10 in accordance with some embodiments. Catheter-based procedure system 10 may be used to perform catheter-based medical procedures, e.g., percutaneous intervention procedures such as PCI (e.g., to treat STEMI), NVI (e.g., to treat an emergent large vessel occlusion (ELVO)), and PVI (e.g., for critical limb ischemia (CLI). Catheter-based medical procedures may include diagnostic catheterization procedures during which one or more catheters or other EMDs are used to aid in the diagnosis of a patient's disease. In one example, a contrast media may be injected into one or more arteries through a catheter and an image of the patient's vasculature is acquired while the contrast media resides therein.

Catheter-based medical procedures may also include catheter-based therapeutic procedures (e.g., angioplasty, stent placement, treatment of peripheral vascular disease, thrombus removal, arterial venous malformation therapy, treatment of aneurysm) in which a catheter (or other EMD) is used to treat a disease. The particular type or nature of EMD used in a catheter-based medical procedure is selected based on the type of procedure that is to be performed. Catheter-based procedure system 10 can perform any number of catheter-based medical procedures using adjustments necessary to accommodate the specific EMDs to be used in the procedures.

Catheter-based procedure system 10 includes, among other elements, bedside unit 20 and control station 26. Bedside unit 20 includes robotic drive 24 and positioning system 22 that are located adjacent to patient 12. Patient 12 is supported on patient table 18. Positioning system 22 is used to position and support robotic drive 24. Positioning system 22 may be, for example, a robotic arm, an articulated arm, a holder, etc. Positioning system 22 may be attached at one end to, for example, a rail on the patient table 18, a base, or a cart. The other end of positioning system 22 is attached to robotic drive 24. Positioning system 22 may be moved out of the way (along with robotic drive 24) to allow for patient 12 to be placed on patient table 18.

Once patient 12 is positioned on patient table 18, positioning system 22 may be used to situate or position robotic drive 24 relative to the patient 12 for the procedure. In some embodiments, patient table 18 is operably supported by pedestal 17, which is secured to the floor and/or earth. Patient table 18 is able to move with multiple degrees of freedom, for example, roll, pitch, and yaw, relative to pedestal 17. Bedside unit 20 may also include operator controls and displays (not shown). For example, such controls and displays may be located on a housing of robotic drive 24.

The term front will refer herein to the side of robotic drive 24 that faces the patient 12 and away from positioning system 22, while the term rear refers to the side of robotic drive 24 that is closest to positioning system 22. The terms top, up, and upper refer to the general direction away from the direction of gravity and the terms bottom, down, and lower refer to the general direction in the direction of gravity.

Generally, robotic drive 24 may be equipped with appropriate EMDs and associated accessories (e.g., embolization coils, liquid embolics, aspiration pumps, contrast injection systems, medicine, hemostasis valve adapters, syringes, stopcocks, inflation device, etc.) to allow operator 11 to perform a catheter-based medical procedure by operating various controls of a control system such as the controls and inputs located at the control station 26. Bedside unit 20, and in particular robotic drive 24, may include any number and/or combination of components to provide bedside unit 20 with the functionality described herein.

Robotic drive 24 includes a plurality of device modules 32, each of which may be controlled to drive a respective EMD. Moreover, each of device modules 32 may be controlled to move linearly toward and away from patient 12. In some embodiments, robotic drive 24 may control one or more of device modules 32 to feed a guidewire into a diagnostic catheter and into a guide catheter in an artery of patient 12. The EMDs enter the body (e.g., a vessel) of patient 12 at an insertion point 16 via, for example, an introducer sheath.

Bedside unit 20 is in communication with control station 26, allowing signals generated by the controls of control station 26 to be transmitted wirelessly or via hardwire to bedside unit 20 to control various functions of bedside unit 20, including functions of the robotic drive 24. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34, or both. Communication between control computing system 34 and various components of catheter-based procedure system 10 may be provided via a communication link that may be a wireless connection, cable connections, or any other means capable of allowing communication to occur between components. Control station 26 or other similar control system may be located either local to or remote from robotic drive 24.

The term local is used to refer to the location of patient 12 and bedside unit 20. The term remote is used to refer to locations that do not have substantially-immediate physical access to bedside unit 20 and/or patient 12. Catheter procedure system 10 may be operated by a control station 26 at the local site, a control station 26 at a remote site, or both a local control station 26 and a remote control station 26 at the same time. At a local site, operator 11 and control station 26 are located in the same room as patient 12 and bedside unit 20 or in an adjacent room.

Control station 26 (and a control computing system) at a remote site may be in communication with the bedside unit 20 and/or a control computing system at a local site using communication systems and services, for example, through the Internet. In some embodiments, the remote site and the local site are in different rooms of the same building, different buildings in the same city, different cities, or other different locations where the remote site does not provide substantially-immediate physical access to bedside unit 20 and/or patient 12.

Control station 26 generally includes one or more input systems 28 including controls configured to receive user manipulations for controlling robotic drive 24 and/or various other components or systems of catheter-based procedure system 10. In the embodiment shown, control station 26 allows operator 11 to control bedside unit 20 to perform a catheter-based medical procedure. For example, input systems 28 may be configured to cause bedside unit 20 to perform various diagnostic or interventional procedures using EMDs controlled by drive mechanisms of robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter).

One or more input systems 28 may include one or more touch screens, joysticks, scroll wheels, and/or buttons. In addition to input systems 28, control station 26 may use additional user controls 44 such as foot switches and microphones for voice commands, etc. Input systems 28 may be configured to instruct advancement, retraction, and/or rotation of EMDs, and activation or deactivation of various components including pumps, valves, switches, clamps, etc.

One or more input systems 28 may include device selection buttons to allow operator 11 to select which of the EMDs loaded into robotic drive 24 are controlled via user manipulation of input controls of one or more input systems 28. Automated routine buttons may be selected to enable algorithmic movements of an EMD without individual direct commands from operator 11. In some embodiments, input systems 28 may include one or more controls or icons (not shown) displayed on a touch screen (e.g., display 30) which, when activated, cause operation of a component of catheter-based procedure system 10.

Display 30 may be configured to display information or patient-specific data to operator 11 located at control station 26. In some embodiments, control station 26 may include two or more displays 30. For example, display 30 may be configured to display image data (e.g., X-ray images, MRI images, CT images, ultrasound images), hemodynamic data (e.g., blood pressure, heart rate), patient record information (e.g., medical history, age, weight), lesion or treatment assessment data (e.g., intravascular ultrasound (IVUS), optical coherence tomography (OCT), fractional flow reserve (FFR)). In addition, display 30 may be configured to display procedure-specific information (e.g., procedural checklist, recommendations, duration of procedure, catheter or guidewire position, aspiration vacuum level, volume of medicine or contrast agent delivered). Further, display 30 may be configured to display information to provide the functionalities associated with a control computing system as will be described below. Display 30 may comprise a touch screen and therefore an input device of system 10.

Catheter-based procedure system 10 also includes imaging system 14. Imaging system 14 may be any medical imaging system usable in conjunction with a catheter-based medical procedure (e.g., non-digital X-ray, digital X-ray, CT, MRI, ultrasound). In some embodiments, imaging system 14 is a digital X-ray imaging device that is in communication with control station 26. Imaging system 14 may include a C-arm that allows imaging system 14 to rotate partially or completely around patient 12 in order to obtain images at different angular positions relative to patient 12 (e.g., sagittal views, caudal views, anterior-posterior views). In some embodiments, imaging system 14 is a fluoroscopy system including a C-arm having an X-ray source 13 and a detector 15, also known as an image intensifier.

Imaging system 14 may be configured to acquire X-ray images of appropriate areas of patient 12 during a procedure. For example, imaging system 14 may be configured to acquire one or more X-ray images of the head to diagnose a neurovascular condition. Imaging system 14 may also be configured to acquire one or more X-ray images (e.g., real time images) during a catheter-based procedure to assist operator 11 to properly position a guidewire, guide catheter, microcatheter, stent retriever, coil, stent, balloon, etc. during the procedure. The acquired image or images may be displayed on display 30. For example, images may be displayed on display 30 to allow operator 11 to accurately move a tip of an aspiration catheter to a position adjacent to a thrombus.

A rectangular coordinate system is hereby introduced including X, Y, and Z axes. The positive X axis is oriented in a longitudinal (axial) distal direction, that is, in the direction from the proximal end to the distal end. The Y and Z axes are in a transverse plane to the X axis, with the positive Z axis oriented up, that is, in the direction opposite of gravity, and the Y axis oriented accordingly based on right-hand rule.

Figure 2:
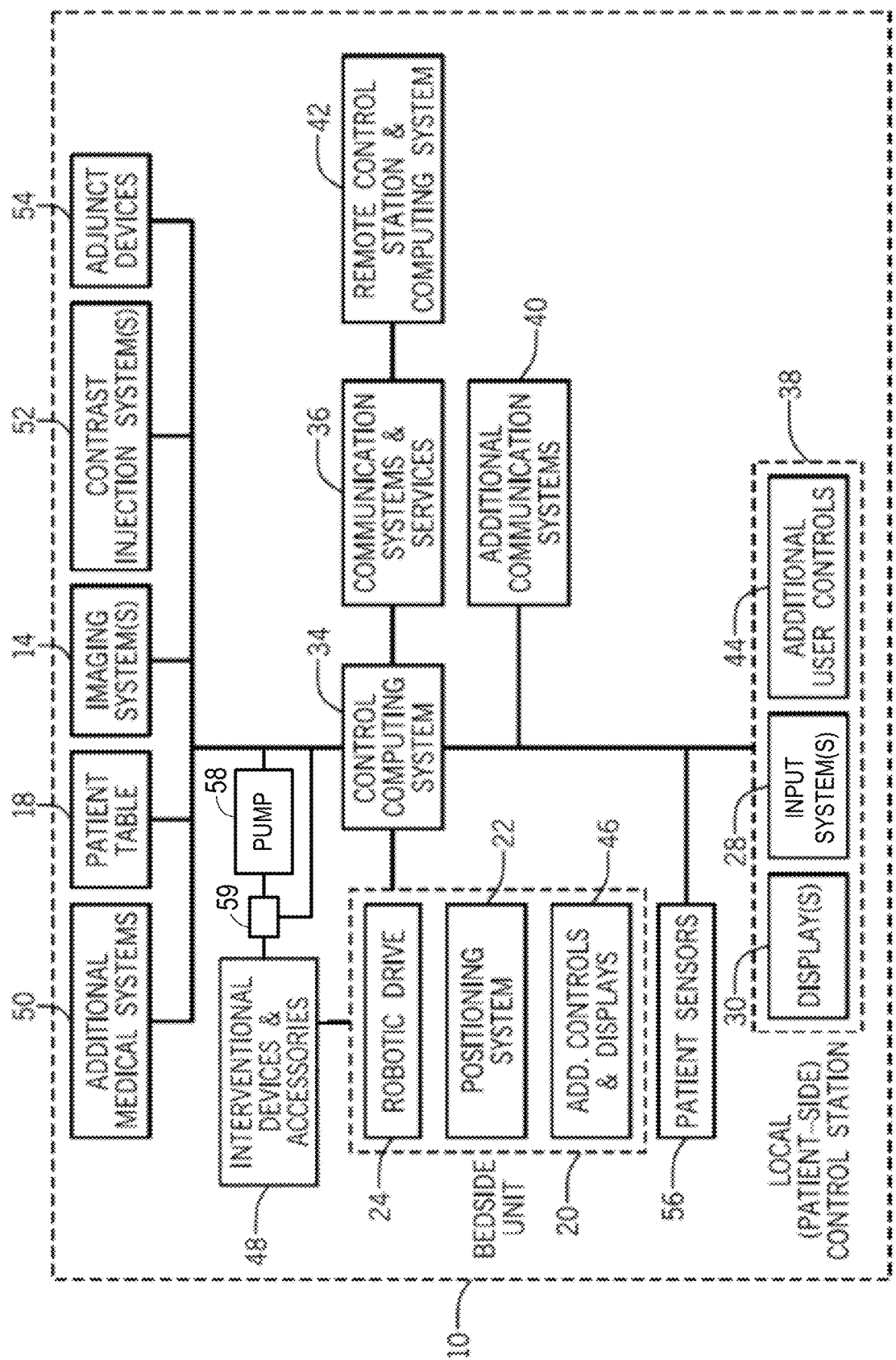
FIG. 2 is a schematic block diagram of a robotic catheter-based procedure system in accordance with some embodiments.

FIG. 2 is a block diagram of catheter-based procedure system 10 in accordance with an exemplary embodiment. Catheter-based procedure system 10 may include a control computing system 34. Control computing system 34 may physically be, for example, part of control station 26. Control computing system 34 may generally comprise a computer processing unit suitable to control catheter-based procedure system 10 as described herein. For example, control computing system 34 may be an embedded system, a dedicated circuit, a general-purpose processor executing program code, etc. Control computing system 34 is in communication with bedside unit 20, communications systems and services 36 (e.g., Internet, firewalls, cloud services, session managers, a hospital network), local control station 38, additional communications systems 40 (e.g., a telepresence system), remote control station and computing system 42, and patient sensors 56 (e.g., electrocardiogram (ECG) devices, electroencephalogram (EEG) devices, blood pressure monitors, temperature monitors, heart rate monitors, respiratory monitors). Control computing system 34 may also be in communication with imaging system 14, patient table 18, additional medical systems 50, contrast injection systems 52 and adjunct devices 54 (e.g., IVUS, OCT, FFR).

As described above, bedside unit 20 includes robotic drive 24, positioning system 22, and additional controls and displays 46. Additional controls and displays 46 may be located on a housing of robotic drive 24. Interventional devices and accessories 48 (e.g., guidewires, catheters) interface to bedside system 20. In some embodiments, interventional devices and accessories 48 may include specialized devices (e.g., IVUS catheter, OCT catheter, FFR wire, diagnostic catheter for contrast) which interface to their respective adjunct devices 54 (e.g., an IVUS system, an OCT system, an FFR system).

In various embodiments, control computing system 34 is configured to receive and generate control signals based on user manipulation of the controls of one or more input systems 28 of local control station 38. Remote control station and computing system 42 may include similar components to the local control station 38. Remote 42 and local 38 control stations can be different and tailored based on their required functionalities. Additional user controls 44 may include, for example, one or more foot input controls. A foot input control may be configured to allow an operator to select functions of imaging system 14 such as turning an X-ray source on and off and scrolling through different stored images. In another embodiment, a foot input may be configured to allow an operator to select which EMDs are mapped to which controls of input system 28. Additional communication systems 40 (e.g., audio conference, video conference, telepresence) may be employed to assist operator interaction with the patient, medical staff (e.g., angiosuite staff), and/or equipment in the vicinity of the bedside.

Control computing system 34 is also in communication with pump 58 and vacuum control 59. Pump 58 may comprise any source for generating a vacuum suitable for thrombus aspiration. In some embodiments, control 59 may be operable to selectively place pump 58 in fluid communication with a lumen of an aspiration catheter of interventional devices and accessories 48.

According to some embodiments, operator 11 operates input systems of remote control station 42 to control robotic drive 24 to position an aspiration catheter in a first position with respect to a thrombus within a patient vessel. Specific examples of such positioning involving manipulation of multiple EMDs in a prescribed sequence will be described herein. The aspiration catheter is coupled to vacuum control 59 which in turn is coupled to pump 58 via tubing. Vacuum control 59 prevents fluid communication between the lumen of the aspiration catheter and the lumen of the tubing. Vacuum control 59 may comprise a clamp, a valve or any other one or more suitable devices.

Control computing system 34 controls pump 58 to initiate evacuation of the tubing lumen which is coupled to vacuum control 59. In some embodiments, control computing system 34 determines that a pressure within the tubing lumen is equal to or less than a target aspiration pressure. In response to the determination, control computing system 34 controls vacuum control 59 to establish fluid communication between the tubing lumen and the aspiration catheter lumen (e.g., by opening the valve, clamp, or other devices of control 59). This action may serve to pull (i.e., suck) the thrombus into the aspiration catheter.

In further embodiments, control computing system 34 determines (e.g., via communication with pump 58) that the pressure within the tubing lumen is greater than a second pressure and, in response, controls vacuum control 59 to terminate fluid communication between the tubing lumen and the aspiration catheter lumen. This action may avoid additional aspiration that is not needed to remove the thrombus.

Alternatively, control computing system 34 instructs local control station 38 or remote control station 40 that the pressure within the tubing lumen is equal to or less than the target aspiration pressure, and this information is presented to operator 11 via, e.g., display 30. Operator 11 may then transmit a command (e.g., using one or more input systems 28) to control computing system 34 to automatically establish fluid communication between the tubing lumen and the aspiration catheter lumen. Similarly, operator 11 may be presented with an indication that the pressure within the tubing lumen is greater than the second pressure and, in response operator 11 may transmit a command to control computing system 34 to terminate fluid communication between the tubing lumen and the aspiration catheter.

According to still further embodiments, after automatically establishing fluid communication between the tubing lumen and the aspiration catheter, and before determining whether the pressure within the tubing lumen is greater than a second pressure, control computing system 34 may determine that the pressure within the tubing lumen is within a predefined range. If it is determined that the pressure within the tubing lumen is within the predefined range, control computing system 34 may instruct robotic drive 24 to adjust the position of the aspiration catheter lumen (e.g., per a pre-programmed sequence of movements that may or may not take into account intermediate pressure changes) until the pressure within the tubing lumen is less than a threshold aspiration pressure.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, or systems to restrict access or use of catheter-based procedure system 10. It should be noted that any of the determinations attributed herein to control computing system 34 may be performed by any suitable component of or connected to system 10.

As mentioned, control computing system 34 is in communication with bedside unit 20 which includes robotic drive 24, positioning system 22 and may include additional controls and displays 46. Control computing system 34 may receive signals from remote control station 42 based on user manipulation of controls of an input system of remote control station 42, and may provide corresponding control signals to bedside unit 20 to control the operation of the motors and drive mechanisms used to drive corresponding EMDs in various degrees of freedom. The various drive mechanisms may be provided as part of robotic drive 24.

Figure 3:
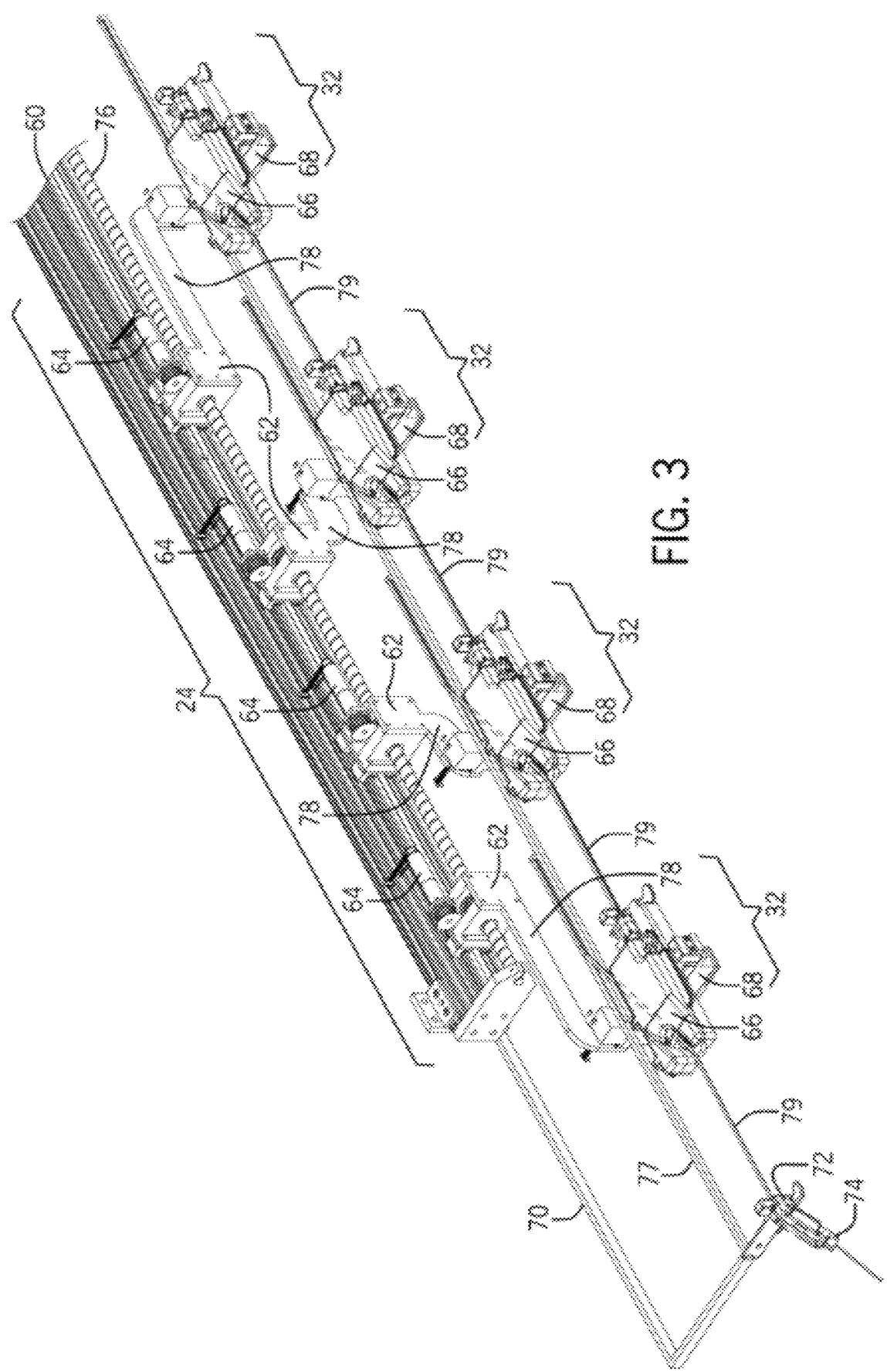
FIG. 3 is a perspective view of a robotic drive for a robotic catheter-based procedure system in accordance with an embodiment.

FIG. 3 is a perspective view of robotic drive 24 for catheter-based procedure system 10 in accordance with some embodiments. Embodiments are not limited to the robotic drive 24 of FIG. 3. Robotic drive 24 of FIG. 3 includes multiple device modules 32a-d coupled to linear member 60. Each device module 32a-d is coupled to linear member 60 via respective stage 62a-d moveably mounted to linear member 60. A device module 32a-d may be connected to a stage 62a-d using a connector such as an offset bracket 78a-d. In another embodiment, a device module 32a-d is directly mounted to a stage 62a-d. Each stage 62a-d may be independently actuated to move linearly along linear member 60. Accordingly, each stage 62a-d (and corresponding device module 32a-d coupled to stage 62a-d) may independently move relative to each other and linear member 60.

A drive mechanism is used to actuate each stage 62a-d. In the embodiment shown in FIG. 3, the drive mechanism includes independent stage translation motors 64a-d coupled to each stage 62a-d and stage drive mechanism 76, for example, a lead screw via a rotating nut, a rack via a pinion, a belt via a pinion or pulley, a chain via a sprocket, or stage translation motors 64a-d may be linear motors themselves. In some embodiments, stage drive mechanism 76 may be a combination of these mechanisms, for example, each stage 62a-d could employ a different type of stage drive mechanism. In some embodiments where the stage drive mechanism is a lead screw and rotating nut, the lead screw may be rotated and each stage 62a-d may engage and disengage from the lead screw to enable movement thereof, e.g., to advance or retract. In the embodiment shown in FIG. 3, stages 62a-d and device modules 32a-d are in a serial drive configuration.

Each device module 32a-d includes device module 68a-d and cassette 66a-d mounted on and coupled to the device module 68a-d. In the embodiment shown in FIG. 3, each cassette 66a-d is mounted to device module 68a-d in a vertical orientation. In other embodiments, each cassette 66a-d may be mounted to device module 68a-d in other mounting orientations. Each cassette 66a-d is configured to interface with and support a proximal portion of an EMD (not shown). In addition, each cassette 66a-d may include elements to provide one or more degrees of freedom in addition to the linear motion provided by the actuation of the corresponding stage 62a-d to move linearly along the linear member 60. For example, a cassette 66a-d may include elements that may be used to rotate an EMD supported therein when the cassette is coupled to the device module 68a-d. Each device module 68a-d includes at least one coupler to provide a drive interface to the mechanisms in each cassette 66a-d to provide the additional degree of freedom. Each cassette 66a-d also includes a channel in which a device support 79a-d is positioned, and each device support 79a-d is used to prevent an EMD from buckling.

A support arm 77a, 77b, and 77c is attached to each device module 32a, 32b, and 32c, respectively, to provide a fixed point for support of a proximal end of the device supports 79b, 79c, and 79d, respectively. Robotic drive 24 may also include device support connection 72 connected to device support 79, distal support arm 70 and support arm 770. Support arm 770 is used to provide a fixed point for support of the proximal end of the distal-most support arm 79a housed in the distal most device module 32a. In addition, introducer interface support (redirector) 74 may be connected to device support connection 72 and an EMD (e.g., an introducer sheath). The configuration of robotic drive 24 has the benefit of reducing volume and weight of robotic drive 24 by using actuators on a single linear member.

To prevent contaminating a patient with pathogens, healthcare staff use aseptic technique in a room housing bedside unit 20 and patient 12. A room housing bedside unit 20 and patient 12 may be, for example, a cath lab or an angio suite. Aseptic technique consists of using sterile barriers, sterile equipment, proper patient preparation, environmental controls and contact guidelines. Accordingly, all EMDs and interventional accessories may be sterilized and allowed contact with either sterile barriers or sterile equipment. In some embodiments, a sterile drape (not shown) is placed over non-sterile robotic drive 24. Each cassette 66a-d is sterilized and acts as a sterile interface between draped robotic drive 24 and at least one EMD. Each cassette 66a-d can be designed to be sterile for single use or to be re-sterilized in whole or part so that a cassette 66a-d or its components can be used in multiple procedures.

As used herein, the term cassette generally refers to a component of a robotic drive system including components to support and move (e.g., rotate and/or translate) at least one EMD. A device module generally refers to a component of a robotic drive system that includes one or more motors with drive couplers which interface with the EMD-moving elements of the cassette. A cassette may provide a sterile interface between at least one EMD and a device module directly or through a device adapter. The term drive module refers to the combination of a device module and a cassette.

In some embodiments, an EMD is a catheter having a hub at a proximal end of the catheter and a flexible shaft extending from the hub toward the distal end of the catheter, wherein the shaft is more flexible than the hub. In one embodiment, a catheter includes an intermediary portion that transitions between the hub and the shaft which includes an intermediate flexibility that is less rigid than the hub and more rigid than the shaft. In some embodiments the intermediary portion is a strain relief.

The longitudinal axis of a member (for example, an EMD or other element in the catheter-based procedure system) is the line or axis along the length of the member that passes through the center of the transverse cross section of the member in the direction from a proximal portion of the member to a distal portion of the member. For example, the longitudinal axis of a guidewire is the central axis in the direction from a proximal portion of the guidewire toward a distal portion of the guidewire even though the guidewire may be non-linear in the relevant portion.

Axial movement of a member refers to translation of the member along the longitudinal axis of the member. For example, when the distal end of an EMD is axially moved in a distal direction along its longitudinal axis into or further into the patient, the EMD is being advanced. When the distal end of an EMD is axially moved in a proximal direction along its longitudinal axis out of or further out of the patient, the EMD is being withdrawn.

In this regard, axial insertion refers to inserting a first member into a second member along the longitudinal axis of the second member. For example, an EMD that is axially loaded in a collet is axially inserted in the collet. An example of axial insertion could be referred to as back loading a catheter on the proximal end of a guidewire. Lateral insertion refers to inserting a first member into a second member along a direction in a plane perpendicular to the longitudinal axis of the second member. Lateral insertion can also be referred to as radial loading or side loading.

Rotational movement of a member refers to the change in angular orientation of the member about the local longitudinal axis of the member. For example, rotational movement of an EMD corresponds to clockwise or counterclockwise rotation of the EMD about its longitudinal axis due to an applied torque. Continuous motion refers to motion that does not require a reset and is uninterrupted, while discrete motion refers to motion that requires a reset and is interrupted.

The terms distal and proximal define relative locations of two different features. With respect to a robotic drive, the terms distal and proximal are defined by the position of the robotic drive in its intended use relative to a patient.

When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient. Similarly, the proximal feature is the feature that is farther from the patient than the distal feature when the robotic drive in its intended in-use position.

When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction. For example, referring to FIG. 1, a robotic device is shown from the viewpoint of an operator facing a patient. In this arrangement, the distal direction is along the positive X coordinate axis and the proximal direction is along the negative X coordinate axis.

With respect to movement of modules, and referring to FIG. 3, an EMD is moved in a distal direction on a path toward a patient through introducer interface support 74 which defines the distal end of robotic drive 24. The proximal end of robotic drive 24 is the point furthest from the distal end along the negative X axis.

With respect to positions of the individual modules, and also referring to FIG. 3, the most distal device module is device module 32*a* closest to the distal end of robotic drive 24. The most proximal device module is device module 32*d* positioned furthest from the distal end of robotic drive 24 along the negative X axis. The relative position of device modules is determined by their relative location to the distal end of the robotic drive. For example, device module 32*b* is distal to device module 32*c*.

With respect to distal/proximal portions, sections or ends of an EMD or the robotic drive, the portions of cassette 66*a* and device module 68*a* are defined by their relative location to the distal end of the robotic drive. For example, the distal end of cassette 66*a* is the portion of the cassette that is closest to the distal end of the robotic drive and the proximal end of cassette 66*a* is the portion of the cassette that is furthest from the distal end of the robotic drive along the negative X axis when the cassette is in-use position on device module 68*a*. Stated in another way, the distal end of cassette 66*a* is the portion of the cassette through which an EMD is closest to the path leading to a patient in the in-use position.

As previously discussed, embodiments of a control station such as control station 26 may include a variety of different input systems for controlling bedside unit 20. Input systems can include a variety of different input controls (e.g., buttons, scroll wheels, joysticks, touch screens) that can be manipulated by a user to control (or, instruct) operation of robotic drive 24. These input controls can be arranged in different layouts or patterns on the input system to facilitate desired functions and cooperative sequencing thereof to perform a desired task requiring independent (and sometimes simultaneous) movement of multiple EMDs.

Additionally, embodiments of an input system can be configured to operate in a variety of different control modes. The functions assigned to one or more controls of an input system in a first control mode may differ from the functions assigned to the one or more controls in a second control mode, and control modes may be selected based on the procedure being performed, the device or devices to be controlled, operator preferences, or any other factors. An input system can be configured to switch between different control modes in response to input from an operator or from control computing system 34.

An input system as described herein may be fixed to, integrated with, or simply rested atop a surface of control station 26. As described herein, an input system may comprise a single integrated housing or multiple independently-movable housings.

Figure 4:
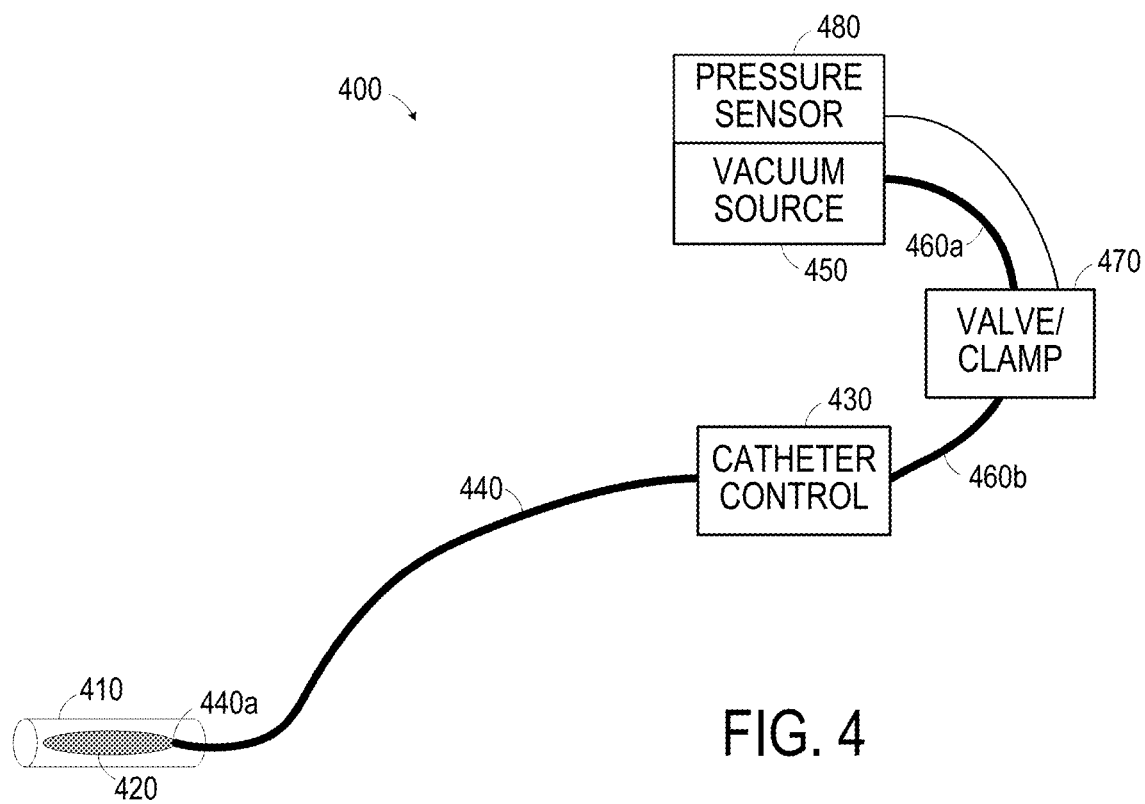
FIG. 4 is a schematic diagram of a thrombectomy system according to some embodiments.

FIG. 4 is a schematic diagram of a thrombectomy system according to some embodiments. Each component of system 400 may be implemented by one or more devices comprised of any suitable combination of hardware and/or software, and two or more illustrated components may be implemented by a same device(s).

FIG. 4 shows vessel 410, which may comprise a vein or artery internal to a patient body. Vessel 420 may be located at any position within a patient. Thrombus 420 is disposed within vessel 410. Embodiments are not limited to a thrombus and vessel of relative sizes and shapes shown in FIG. 4 or in any subsequently-described figures. Embodiments are also not limited to a single substantially-contiguous thrombus.

Catheter control 430 operates to navigate catheter 440 to thrombus 420 within vessel 410. As shown, catheter control 430 has maneuvered tip 440*a* of catheter 440 to a position adjacent to thrombus 420 within vessel 410. Catheter 440 may comprise any EMD defining a lumen in which negative pressure may be generated. Catheter 440 may comprise a purpose-designed aspiration catheter defining a catheter lumen.

As will be described below, catheter control 430 may manipulate (i.e., advance/retract/rotate) one or more unshown guidewires and catheters in order to navigate catheter 440 to the illustrated position. Such navigation may be facilitated using a robotic drive such as but not limited to robotic drive 24. Accordingly, in some embodiments, catheter control 430 comprises catheter-based procedure system 10.

Vacuum source 450 may comprise a pump or other device suitable for generating negative pressure in an interventional theatre. According to system 400, vacuum source 450 is coupled to tubing 460*a* which is coupled to valve/clamp 470. Valve/clamp 470 is coupled to tubing 460*b* which is coupled to catheter 440 via catheter control 430. Tubing 460*a* and tubing 460*b* may comprise any tubing suitable for thrombus aspiration as described therein, and together comprise a tubing lumen.

When valve/clamp 470 is closed, negative pressure generated by vacuum source 450 exists within a lumen of tubing 460*a* but not within a lumen of tubing 460*b* (and therefore not within catheter 440). When valve/clamp 470 is open, vacuum source 450, the lumen of tubing 460*a*, the lumen of tubing 460*b* and the lumen of catheter 440 are all in fluid communication with one another. Accordingly, any negative pressure generated by vacuum source 450 is experienced at tip 440*a* of catheter 440.

According to system 400, pressure sensor 480 is coupled to or integrated with vacuum source 450. Pressure sensor 480 may determine a pressure generated by vacuum source 450, for example a pressure generated within tubing 460*a* while valve/clamp 470 is closed. Valve/clamp 470 may monitor this pressure via communication with pressure sensor 480 and determine whether to open or close itself based thereon.

For example, in some embodiments, catheter control 430 manipulates a series of EMDs under control of an operator to position tip 440*a* of catheter 440 adjacent to thrombus 420. Next, tubing 460*b* is coupled, either manually or via mechanisms of catheter control 430, to catheter 440 such that tubing 460*b* and catheter 440 are in fluid communication with one another. Vacuum source 450 is operated (e.g., via a command from catheter control 430 or an operator) to begin generation of negative pressure within tubing 460*a*.

Valve/clamp 470 monitors pressure determined by pressure sensor 480 until it is determined that a pressure within tubing 460*a* is equal to or less than a target aspiration pressure. Alternatively, pressure sensor 480 may provide a signal to valve/clamp 470 once pressure sensor 480 determines that a pressure within tubing 460*a* is equal to or less than a target aspiration pressure. In either case, in response to the determination, valve/clamp 470 is opened to automatically establish fluid communication between tubing 460*a*, tubing 460*b* and catheter 440. Consequently, thrombus 420 may be forcefully removed from vessel 410 and drawn into catheter 440.

After opening of valve/clamp 470, valve/clamp 470 may further determine, based on pressure sensor 480, that the pressure within tubing lumen 460*a* is greater than a second pressure and, in response, close itself to automatically terminate fluid communication between tubing lumen 460*a* and catheter 440. Such a procedure may serve to detect completion of the removal of thrombus 420 and to accordingly terminate aspiration.

In still further embodiments, after opening of valve/clamp 470 but before closing valve/clamp 470 because the pressure within tubing lumen 460*a* is greater than a second pressure, valve/clamp 470 determines based on pressure sensor 480 that the pressure within tubing lumen 460*a* is within a predefined range. The predefined range is higher than the first pressure and lower than the second pressure and is intended to indicate the existence of some resistance to suction into catheter 440 but not to the extent expect if tip 440*a* were positioned against thrombus 420. If it is determined that the pressure within tubing lumen 460*a* is within the predefined range, valve/clamp 470 (or pressure sensor 480, for example) may communicate with catheter control 430 to change the position (e.g., rotate) catheter 440 until the pressure within tubing lumen 460*a* is equal to or less than a desired pressure.

In some embodiments, valve/clamp 470 is a component of catheter control 430. Accordingly, a single section of tubing might extend from vacuum source 450 to such a valve/clamp 470, which is then directly coupled to catheter 440 by catheter control 430.

Figure 5:
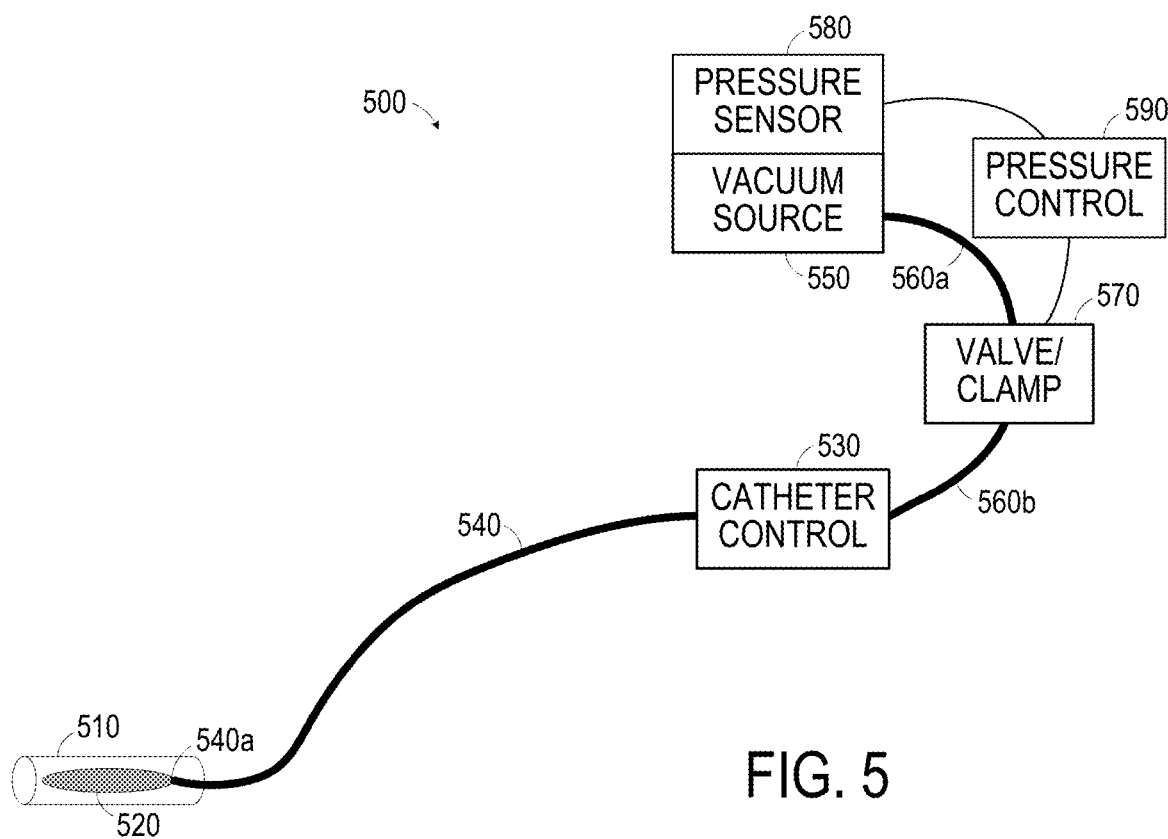
FIG. 5 is a schematic diagram of a thrombectomy system according to some embodiments.

FIG. 5 is a schematic diagram of a thrombectomy system according to some embodiments. System 500 includes vessel 510 and thrombus 520 disposed within vessel 510 as described above. Catheter control 530 operates to navigate catheter 540 to thrombus 520 as described with respect to catheter control 430 and catheter 440.

Vacuum source 550, tubing 560*a*, tubing 560*b*, valve/clamp 570 and pressure sensor 580 may be configured as described above with respect to similarly-named elements of system 400. System 500 also includes pressure control 590 disposed between pressure sensor 580 and valve/clamp 570. Pressure control 590 may execute the determinations and control of valve/clamp 570 which was attributed above to valve/clamp 470. Generally, pressure control 590 may monitor the pressure within tubing lumen 560*a* via communication with pressure sensor 580 and instruct valve/clamp 570 to open or close based thereon. In some embodiments, pressure control 590 is a component of catheter control 530. In this regard, pressure control 590 may comprise control computing system 34 of system 10.

Pressure control 590 may initiate operation of vacuum source 550 to begin generation of negative pressure within tubing 560*a*. Pressure control 590 monitors pressure determined by pressure sensor 580 until a pressure within tubing 560*a* is equal to or less than a target aspiration pressure. In response to this determination, pressure control 590 instructs valve/clamp 570 to open to automatically establish fluid communication between tubing 560*a*, tubing 560*b* and catheter 540.

Subsequent to this opening of valve/clamp 570, pressure control 590 may further monitor pressure determined by pressure sensor 580 until a pressure within tubing 560*a* is greater than a second pressure and, in response, instruct valve/clamp 570 to close itself to automatically terminate fluid communication between tubing lumen 560*a* and catheter 540. Additionally, if pressure control 590 determines that the pressure within tubing lumen 560*a* is within a predefined range higher than the first pressure and lower than the second pressure, pressure control 590 may communicate with catheter control 530 to change the position of (e.g., rotate) catheter 540 until the pressure within tubing lumen 560*a* is equal to or less than the first pressure.

Figure 6:
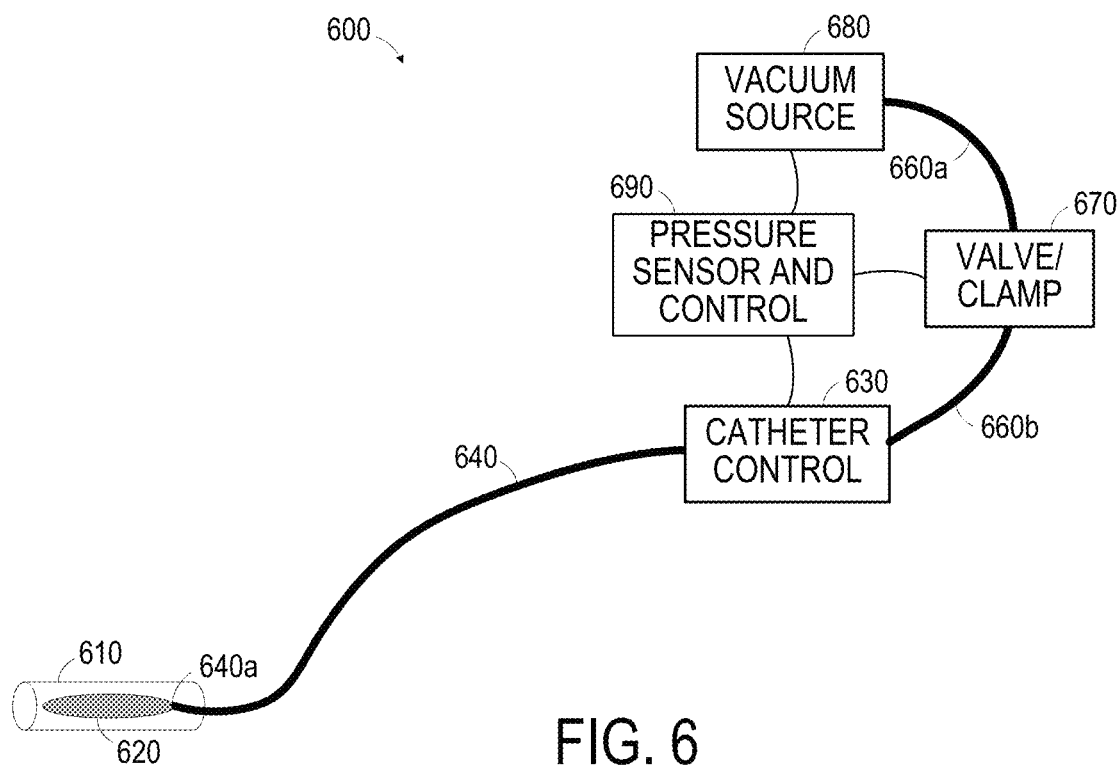
FIG. 6 is a schematic diagram of a thrombectomy system according to some embodiments.

FIG. 6 is a schematic diagram of a thrombectomy system according to some embodiments. System 600 is similar to system 500 of FIG. 5, except that the above-described functions of pressure sensor 580 and pressure control 590 are combined within pressure sensor and control 690. Vacuum source 680, tubing 660*a*, tubing 660*b*, valve/clamp 670 and catheter control 630 may be configured as described above with respect to similarly-named elements of system 500.

Pressure sensor and control 690 may monitor the pressure within tubing lumen 660*a* via communication with vacuum source 680 and instruct valve/clamp 670 to open or close based thereon. As mentioned with respect to pressure control 590 of system 500, in some embodiments, pressure sensor and control 690 is a component of catheter control 630. For example, pressure sensor and control 690 may comprise control computing system 34 of system 10.

Pressure sensor and control 690 may initiate operation of vacuum source 680 to begin generation of negative pressure within tubing 660a. Pressure sensor and control 690 monitors pressure generated by vacuum source 680 (e.g., by communication with vacuum source 680 which includes a pressure sensor, by optical sensing of tubing 660a) until it is determined that a pressure within tubing 660a is equal to or less than a target aspiration pressure. In response to this determination, pressure sensor and control 690 instructs valve/clamp 670 to open to automatically establish fluid communication between tubing 660a, tubing 560b and catheter 640.

Next, pressure sensor and control 690 may determine that a pressure within tubing 660a has become greater than a second pressure and, in response, instruct valve/clamp 670 to close itself to automatically terminate fluid communication between tubing lumen 660a and catheter 640. If, between the opening and closing of valve/clamp 670 as described above, pressure sensor and control 690 determines that the pressure within tubing lumen 660a is within a predefined range higher than the first pressure and lower than the second pressure, pressure sensor and control 690 may communicate with catheter control 630 to change the position of (e.g., rotate) catheter 640 until the pressure within tubing lumen 660a is equal to or less than the first pressure.

Figure 7:
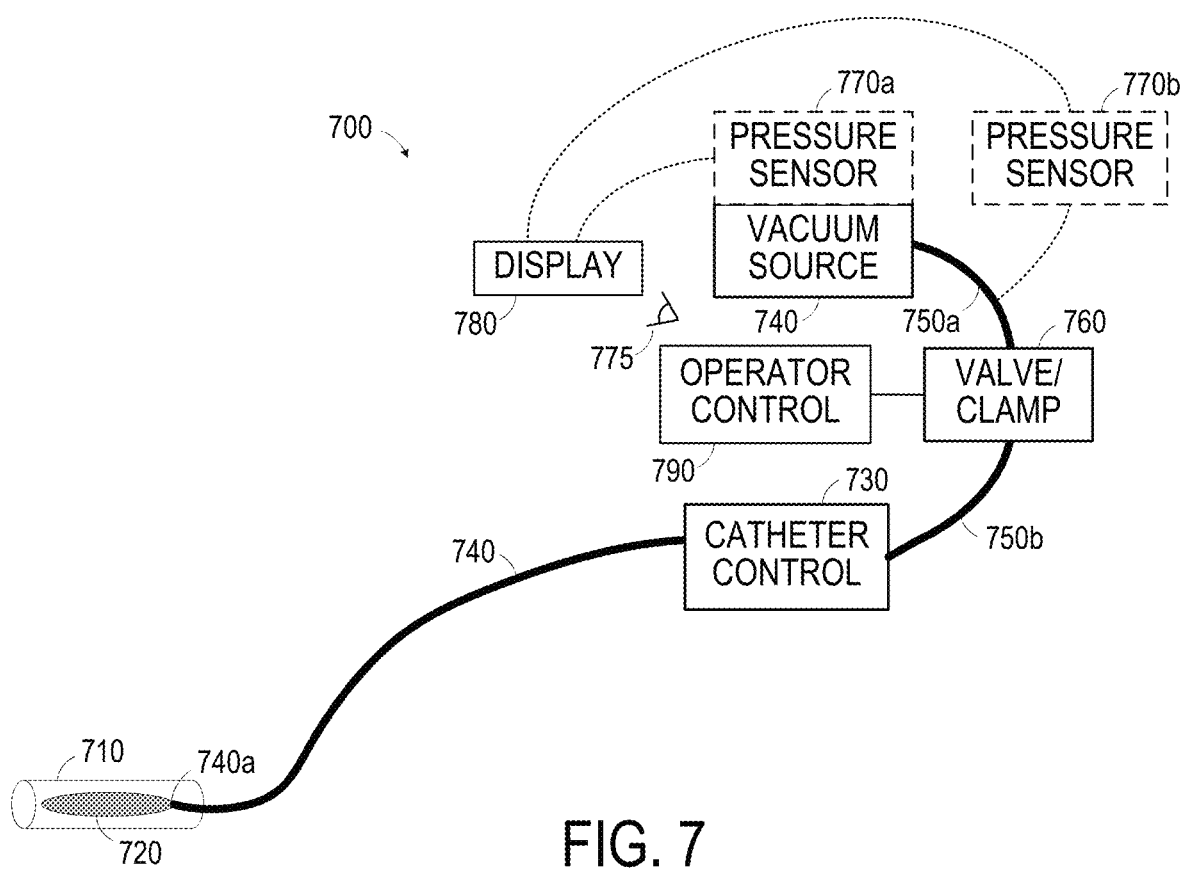
FIG. 7 is a schematic diagram of a thrombectomy system according to some embodiments.

FIG. 7 is a schematic diagram of a thrombectomy system according to some embodiments. System 700 includes presentation of pressure-based indications to an operator, and subsequent operator control of system 700. System 700 is presented in two alternative arrangements, a first in which pressure sensor 770a is coupled to or integrated with vacuum source 740, and a second in which pressure sensor 770b is separate from vacuum source 740. Pressure sensor 770b may determine a pressure within tubing 750a via optical means, a sensor element within tubing 750a, or any other suitable technique.

Regardless of the implementation of the pressure sensor (e.g., pressure sensor 770a or pressure sensor 770b), system 700 includes presentation of an indication of the pressure within tubing 750a to operator 775 via display 780. Although FIG. 7 shows a direct communication link between pressure sensor 770a/pressure sensor 770b and display 780, the pressure may be transmitted from pressure sensor 770a/pressure sensor 770b to display 780 via any number of intermediary components, such as, for example, control computing system 34.

In operation, operator 775 operates catheter control 730 (e.g., of a catheter-based robotic procedure system such as system 10) to position catheter 740 with respect to thrombus 720 within vessel 710. Once the position is satisfactory to operator 775, operator 775 initiates operation of vacuum source 740 to begin generation of negative pressure within tubing 750a.

Display 780 presents an indication of the negative pressure to operator 775. The indication may comprise a pressure value and/or an indication that a pressure within tubing 750a is equal to or less than a target aspiration pressure. The indication may simply comprise a notification, presented once a pressure within tubing 750a is equal to or less than the target aspiration pressure, that the system is ready for aspiration. After receiving the indication, operator 775 may manipulate operator control 790 to instruct valve/clamp 760 to open and thereby automatically establish fluid communication between tubing 750a, tubing 750b and catheter 740. Operator control 790 may comprise any of the input systems described herein, including but not limited to a touch screen (e.g., display 780 may also comprise operator control 790), a console button, a foot switch, and a joystick.

After opening of valve/clamp 760, display 780 may further present an indication that a pressure within tubing 750a has become greater than a second pressure. The indication may comprise a notification to terminate aspiration. In response to the indication, operator 775 may manipulate operator control 790 to close valve/clamp 760 to terminate fluid communication between tubing 750a and catheter 740. In some embodiments of system 700, the pressure within tubing 750a is monitored and, once it is determined that the pressure within tubing 750a has become greater than a second pressure, valve/clamp 760 is automatically instructed to close without intervention of operator 775.

Between the aforementioned opening and closing of valve/clamp 760, display 780 may present and indication that the pressure within tubing lumen 750a is within a predefined range higher than the first pressure and lower than the second pressure. The indication may comprise a pressure value and/or a notification to reposition catheter 740 with respect to thrombus 720. Based on the indication, operator 775 may instruct operation of catheter control 730 to reposition catheter 740. The repositioning may comprise a pre-programmed set of movements and/or individual movements instructed by operator 775. In some embodiments, display 780 presents an indication once the pressure within tubing lumen 750a has decreased to equal to or less than the first pressure, at which point operator 775 may cease instruction of catheter control 730.

Figure 8:
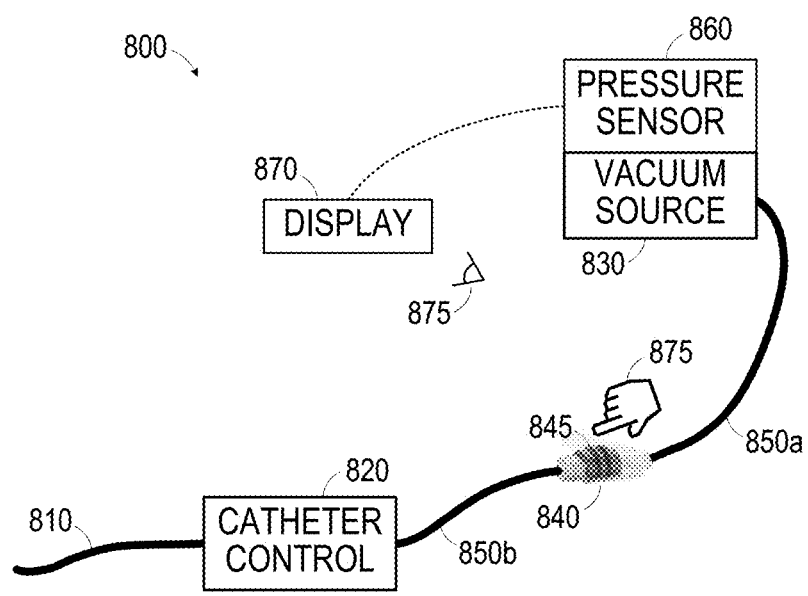
FIG. 8 is a schematic diagram of a thrombectomy system according to some embodiments.

FIG. 8 is a schematic diagram of a thrombectomy system according to some embodiments. System 800 may comprise an implementation of system 700. In particular, valve 840 comprises an implementation of valve/clamp 760. Similar to the description of system 700, operator 875 may operate catheter control 820 to position catheter 810 with respect to a thrombus within a vessel. Once the position is satisfactory, vacuum source 830 is operated to begin generation of negative pressure within tubing 850a.

Display 870 presents an indication of the negative pressure to operator 875. After receiving the indication, operator 875 may directly manipulate valve 740 to open and thereby automatically establish fluid communication between tubing 850a, tubing 850b and catheter 810. In the illustrated embodiment, valve 840 comprises a flow control valve including slider switch 845 which may be operated using one hand to selectively open or close valve 840. Embodiments may employ any suitable device for establishing and terminating fluid communication between two lumens.

Display 780 may further present an indication that a pressure within tubing 750a has become greater than a second pressure. The indication may comprise a notification to terminate aspiration. In response to the indication, operator 775 may manipulate operator control 790 to close valve/clamp 760 to terminate fluid communication between tubing 750a and catheter 740. In some embodiments of system 700, the pressure within tubing 750a is monitored and, once it is determined that the pressure within tubing 750a has become greater than a second pressure, valve/clamp 760 is automatically instructed to close without intervention of operator 775.

Between the aforementioned opening and closing of valve/clamp 760, display 780 may present and indication that the pressure within tubing lumen 750a is within a predefined range higher than the first pressure and lower than the second pressure. The indication may comprise a pressure value and/or a notification to reposition catheter 740 with respect to thrombus 720. Based on the indication, operator 775 may instruct operation of catheter control 730 to reposition catheter 740. The repositioning may comprise a pre-programmed set of movements and/or individual movements instructed by operator 775. In some embodiments, display 780 presents an indication once the pressure within tubing lumen 750a has decreased to equal to or less than the first pressure, at which point operator 775 may cease instruction of catheter control 730.

Figure 9:
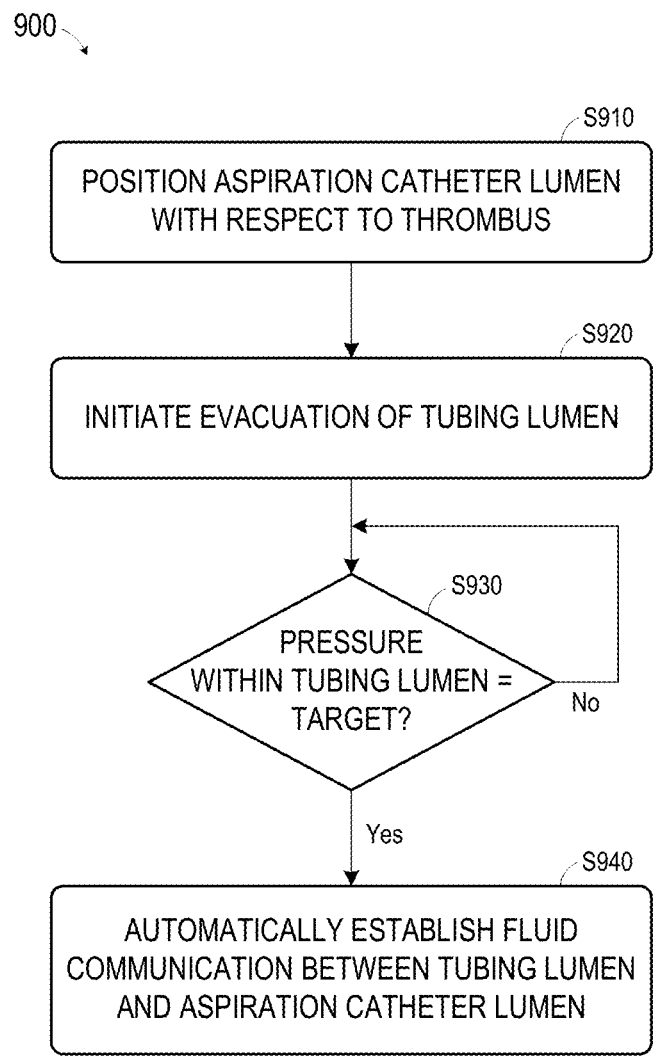
FIG. 9 is a flow diagram of a thrombectomy process according to some embodiments.

FIG. 9 comprises a flow diagram of process 900 to aspirate a thrombus according to some embodiments. Process 900 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

Initially, at S910, an aspiration catheter defining an aspiration catheter lumen is positioned in a first position with respect to a thrombus. For example, an operator may control a robotic drive to manipulate a series of EMDs in a pre-scribed sequence at S910 to position a tip of an aspiration catheter against a thrombus. According to one such pre-scribed sequence, an introducer sheath is inserted into an access site, such as but not limited to a radial or femoral artery. Next, a diagnostic guidewire is inserted into the sheath and is advanced to the base of the skull by a robotic drive in response to operator commands. A guide catheter and base catheter are then advanced (either simultaneously or sequentially) over the diagnostic guidewire to the base of the skull. The diagnostic guidewire and guide catheter are then removed, leaving the base catheter.

A coaxial "stack" consisting of a microwire surrounded by a microcatheter surrounded by an aspiration catheter is then inserted into the base catheter. With the microwire leading, the stack passes the base of the skull (i.e., where the base catheter terminates) and navigates the vasculature until the microwire reaches the thrombus. The aspiration catheter is then advanced, either with or without the microcatheter (i.e., for structural support), until a lumen of the aspiration catheter is in contact with the thrombus. The foregoing process is aided by contemporaneously-acquired and contrast enhanced X-ray images.

Figure 10:
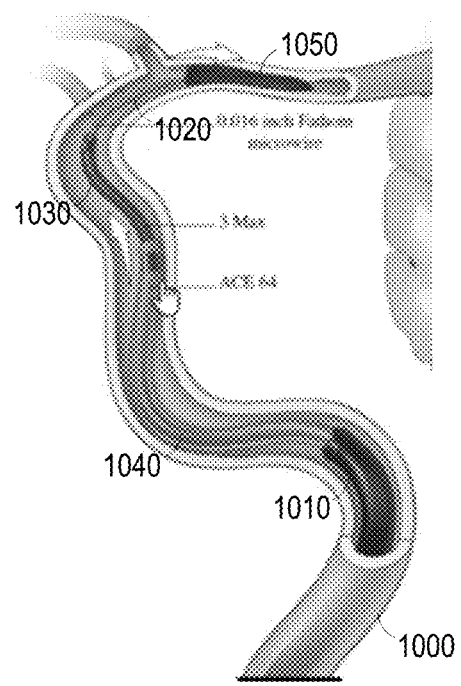
FIG. 10 is a cutaway diagram of a vessel exposing stacked EMDs during a thrombectomy process according to some embodiments.

FIG. 10 illustrates vessel 1000 in which base catheter 1010 resides. A stack consisting of microwire 1020, microcatheter 1030 and aspiration catheter 1040 has passed through base catheter 1010 on the way to thrombus 1050. Microwire 1020 has reached thrombus 1050 and microcatheter 1030 is being advanced over microwire 1020 toward thrombus 1050. Next, aspiration catheter 1040 will be advanced over microcatheter 1030 (and microwire 1020) until aspiration catheter 1040 reaches thrombus 1050. Microwire 1020 and microcatheter 1030 may then be removed from within aspiration catheter 1040.

Returning to process 900, evacuation of a tubing lumen to generate negative pressure therein is initiated at S920. The tubing lumen may be coupled to a pump or other vacuum source as noted above. As also noted, the tubing lumen is not in fluid communication with the aspiration catheter. According to some embodiments, an operator operates an input control associated with a robotic catheter-based procedure system to instruct operation of the vacuum source at S920.

Flow pauses at S930 until the pressure within the tubing lumen is equal to (or less than) a target pressure. The target pressure may be pre-defined and/or set by the operator, and may be determined based on the size and/or shape of the thrombus, the nature of the vessel (e.g., delicate, tortuous, damaged) in which the thrombus resides, or any other factor. Flow proceeds to S940 once is determined that a pressure within the tubing lumen equal to (or less than) the target pressure.

At S940, fluid communication is automatically established between the tubing lumen and the aspiration catheter lumen. Several examples of S940 are described herein. In one example, both the tubing and the aspiration catheter are coupled to either end of a closed valve prior to S940, and S940 includes opening the valve. The valve may be opened via an electromechanical actuator or manually by an operator. Implementations of S940 are not limited to those described herein.

Figure 11:
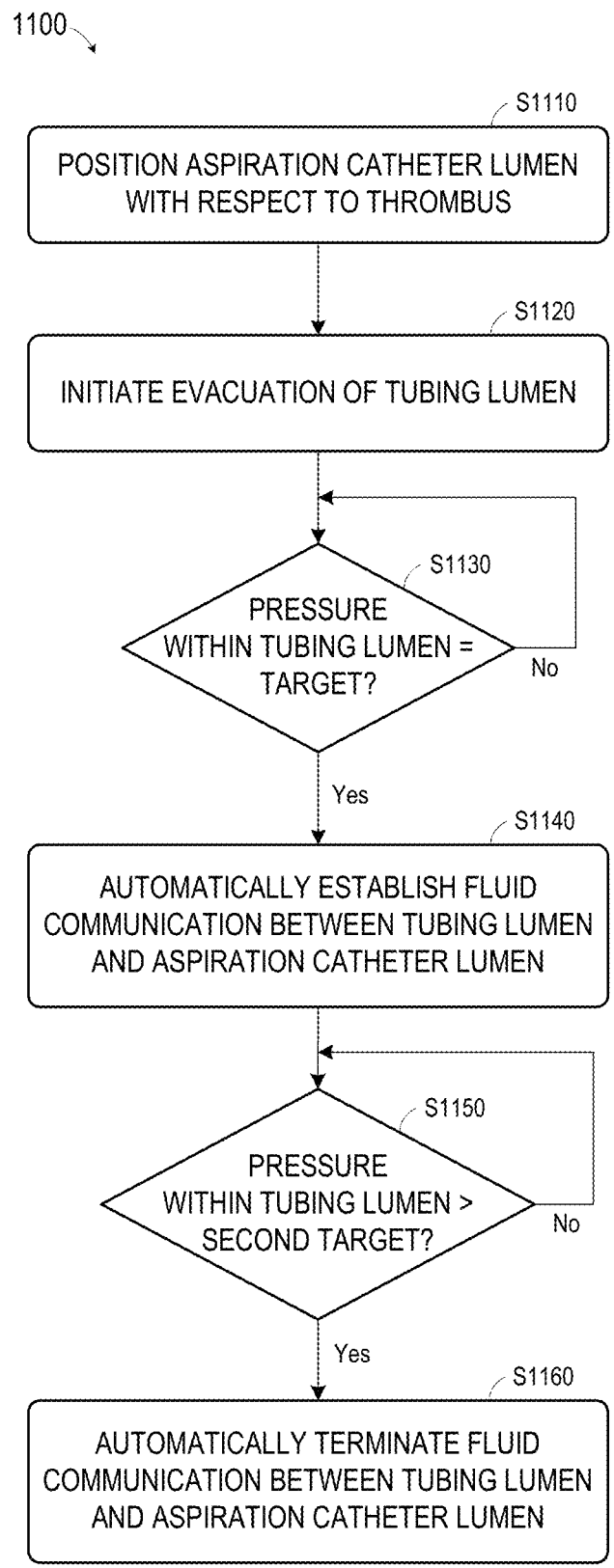
FIG. 11 is a flow diagram of a thrombectomy process according to some embodiments.

S1110 through S1140 of process 1100 of FIG. 11 may proceed similarly to S910 through S940 of process 900. Flow pauses after S1140, at S1150, until it is determined that the pressure within the tubing lumen is greater than (or equal to) a second target pressure. As described above, the second target pressure may be a pressure that is expected in a case that the thrombus has been evacuated from the vessel (and the aspiration catheter).

Flow proceeds to S1160 once the second target pressure is reached. At S1160, the fluid communication between the tubing lumen and the aspiration catheter lumen is terminated. Continuing the above example, S1160 may comprise electromechanical or manual closing of a valve disposed between the tubing lumen and the aspiration catheter lumen.

Figure 12A:
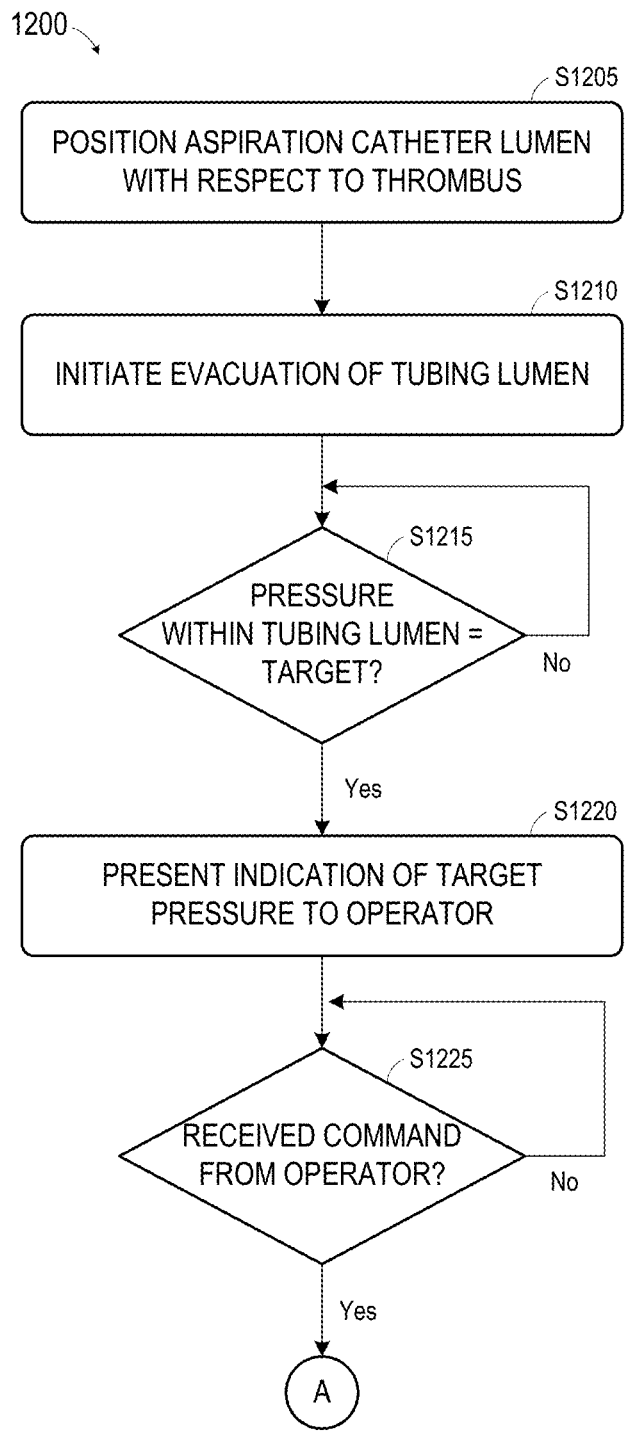
FIGS. 12*a* and 12*b* comprise a flow diagram of a thrombectomy process according to some embodiments.
Figure 12B:
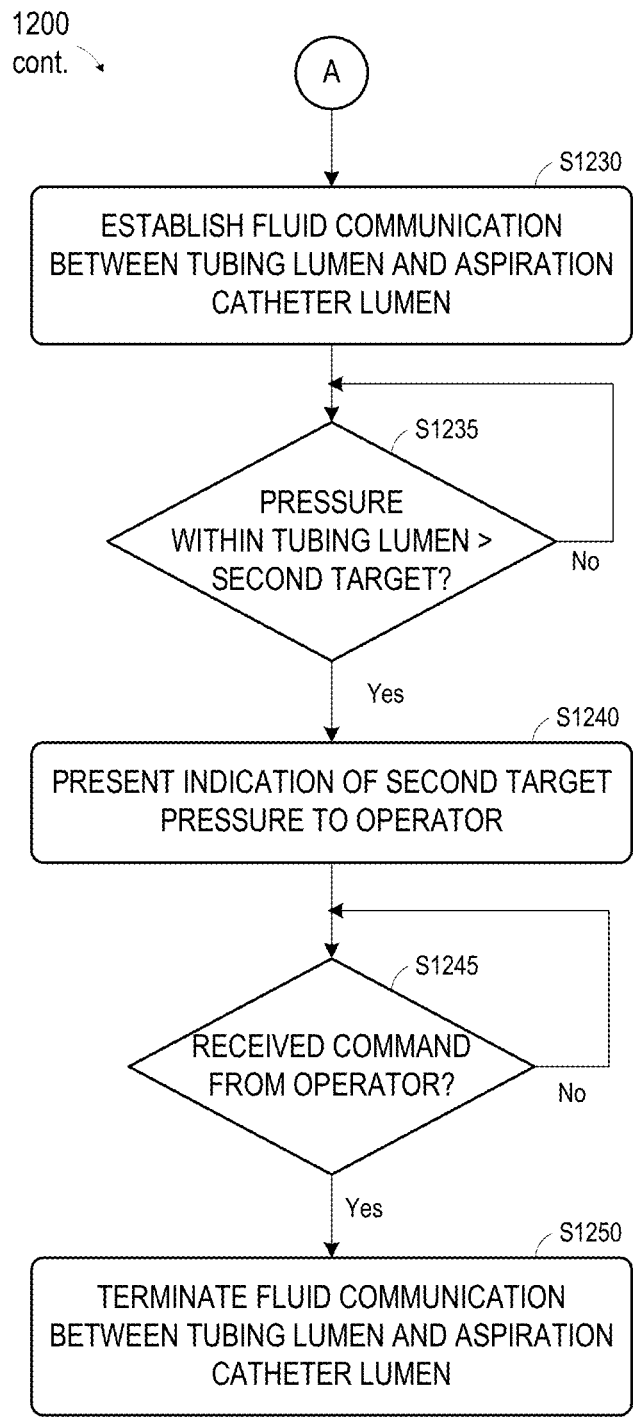

Turning to FIGS. 12, S1205, S1210 and S1215 of process 1200 may proceed similarly to respective ones of S910, S920 and S930 of process 900. At S1220, an indication is presented to an operator, indicating that the pressure within the tubing lumen (i.e., the pressure to be experienced by the aspiration catheter lumen) has reached the target pressure. As described above, the indication may be presented via a display of an operator console, and may be communicated from the vacuum source or a separate pressure sensor to a control computing system which then instructs presentation of the indication.

Flow pauses at S1225 until a command from the operator is received. The target pressure may be maintained during the pause at S1225. The operator may operate an input control of a control console to instruct the system to perform aspiration, in response to which flow proceeds to S1230.

Fluid communication is automatically established between the tubing lumen and the aspiration catheter lumen at S1230. Flow then pauses at S1235 until it is determined that the pressure within the tubing lumen is greater than (or equal to) a second target pressure. Another indication is presented to the operator at S1240, indicating that the pressure within the tubing lumen (and within the aspiration catheter lumen) has reached a second target pressure. Flow pauses at S1245 until a next command from the operator is received.

The operator may operate an input control of the control console at S1245 to instruct the system to terminate aspiration. In response, at S1250, the fluid communication between the tubing lumen and the aspiration catheter lumen is terminated. For example, a valve disposed between the tubing lumen and the aspiration catheter lumen may be closed at S1250.

Figure 13A:
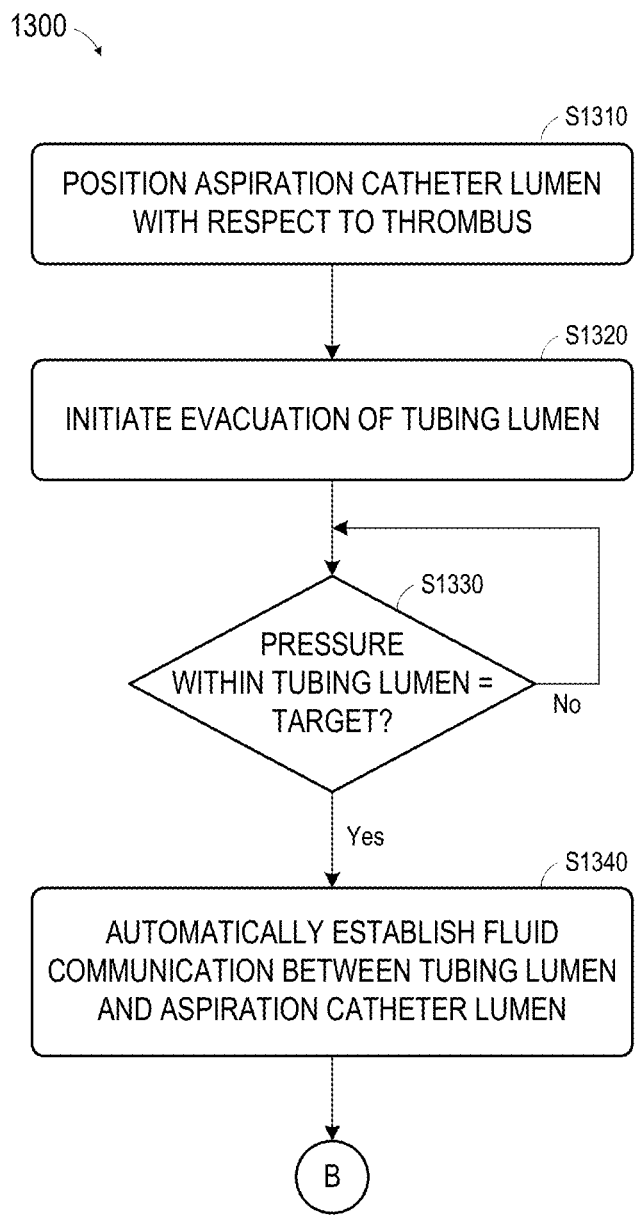
FIGS. 13*a* and 13*b* comprise a flow diagram of a thrombectomy process according to some embodiments.
Figure 13B:
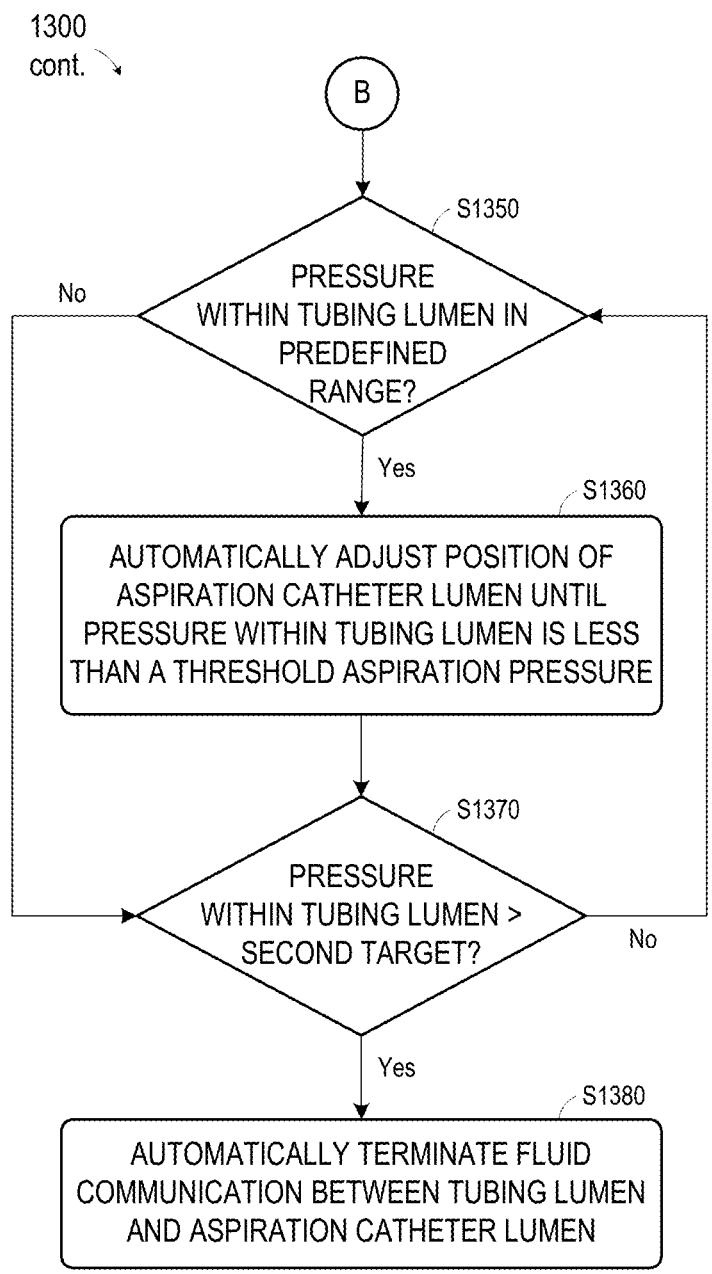

FIG. 13 is a flow diagram of process 1300 according to some embodiments. S1310 through S1340 of process 1300 may proceed similarly to S910 through S940 of process 900. Flow proceeds to S1350 after fluid communication between a tubing lumen and an aspiration catheter is established at S1340.

At S1350, it is determined whether the pressure within the tubing lumen is within a predefined range. As described above, the predetermined range may comprise a predetermined range of pressures which indicate that the aspiration catheter is not engaged against the thrombus in a manner providing suitable suction thereto. Flow proceeds to S1370 if the pressure within the tubing lumen is not within the predefined range.

If it is determined at S1350 that the pressure within the tubing lumen is within the predefined range, the position of the aspiration catheter lumen is automatically adjusted at S1360 until the pressure within the tubing lumen is less than a threshold aspiration pressure. This adjustment may be automatically performed without operator intervention using a set of one or more catheter movements intended to better-position the catheter. In some embodiments, the adjustment is performed under partial or full operator control.

At S1370, it is determined whether the pressure within the tubing lumen is greater than a second pressure. If not, flow returns to S1350 and continues as described above. If so, fluid communication between the tubing lumen and the aspiration catheter lumen is automatically terminated at S1380, using any system described herein or that is known.

Those in the art will appreciate that various adaptations and modifications of the above-described embodiments can be configured without departing from the claims. Therefore, it is to be understood that the claims may be practiced other than as specifically described herein.

What is claimed is:

1. A method comprising:
   receiving a first command to position a catheter lumen in a position with respect to a thrombus, the catheter lumen defined by a catheter; and
   while the catheter lumen is positioned in the position with respect to the thrombus:
     receiving a second command to initiate evacuation of a tubing lumen while the tubing lumen is not in fluid communication with the catheter lumen;
     determining while the tubing lumen is not in fluid communication with the catheter lumen, that a pressure within the tubing lumen is equal to or less than a target aspiration pressure; and
     in response to the determination that the pressure within the tubing lumen is equal to or less than the target aspiration pressure while the tubing lumen is not in fluid communication with the catheter lumen, automatically establishing fluid communication between the tubing lumen and the catheter lumen.

2. A method according to claim 1, further comprising:
   after automatically establishing fluid communication between the tubing lumen and the catheter, determining whether the pressure within the tubing lumen is greater than a second pressure; and
   if it is determined that the pressure within the tubing lumen is greater than the second pressure, automatically terminating fluid communication between the tubing lumen and the catheter lumen.

3. A method according to claim 2, further comprising:
   after automatically establishing fluid communication between the tubing lumen and the catheter and before determining whether the pressure within the tubing lumen is greater than the second pressure, determining whether the pressure within the tubing lumen is within a predefined range; and
   if it is determined that the pressure within the tubing lumen is within the predefined range, automatically adjusting the position of the catheter lumen until the pressure within the tubing lumen is less than a threshold aspiration pressure.

4. A method according to claim 1, further comprising:
   after automatically establishing fluid communication between the tubing lumen and the catheter lumen, determining whether the pressure within the tubing lumen is within a predefined range; and
   if it is determined that the pressure within the tubing lumen is within the predefined range, automatically adjusting the position of the catheter lumen until the pressure within the tubing lumen is less than a threshold aspiration pressure.

5. A method according to claim 1, further comprising:
   after automatically establishing fluid communication between the tubing lumen and the catheter lumen, determining whether the pressure within the tubing lumen is greater than a second pressure; and
   if it is determined that the pressure within the tubing lumen is greater than the second pressure, presenting an indication to an operator;
   after presenting the indication, and while the pressure within the tubing lumen is greater than the second pressure, receiving a command from the operator; and
   in response to receipt of the command, automatically terminating fluid communication between the tubing lumen and the catheter lumen.

6. A method according to claim 5, further comprising:
   after automatically establishing fluid communication between the tubing lumen and the catheter lumen and before determining that the pressure within the tubing lumen is greater than the second pressure, determining whether the pressure within the tubing lumen is within a predefined range; and
   if it is determined that the pressure within the tubing lumen is within the predefined range, automatically adjusting the position of the catheter lumen until the pressure within the tubing lumen is less than a threshold aspiration pressure.

7. A method according to claim 1, wherein automatically establishing fluid communication between the tubing lumen and the catheter lumen comprises:
   presenting a first indication to an operator;
   after presenting the first indication, and while the pressure within the tubing lumen is equal to or less than the target aspiration pressure, receiving a third command from the operator to establish fluid communication between the tubing lumen and the catheter lumen; and
   in response to receipt of the third command, automatically establishing fluid communication between the tubing lumen and the catheter lumen.

8. A method according to claim 7, further comprising:
   after automatically establishing fluid communication between the tubing lumen and the catheter lumen, determining whether the pressure within the tubing lumen is greater than a second pressure; and if it is determined that the pressure within the tubing lumen is greater than the second pressure, presenting a second indication to the operator;

after presenting the second indication, and while the pressure within the tubing lumen is greater than the second pressure, receiving a fourth command from the operator; and in response to receipt of the fourth command, automatically terminating fluid communication between the tubing lumen and the catheter lumen.

9. A method according to claim 8, further comprising:

after automatically establishing fluid communication between the tubing lumen and the catheter lumen and before determining that the pressure within the tubing lumen is greater than the second pressure, determining whether the pressure within the tubing lumen is within a predefined range; and if it is determined that the pressure within the tubing lumen is within the predefined range, automatically adjusting the position of the catheter lumen until the pressure within the tubing lumen is less than a threshold aspiration pressure.

10. A method according to claim 8, further comprising:

after automatically establishing fluid communication between the tubing lumen and the catheter lumen and before determining that the pressure within the tubing lumen is greater than the second pressure, determining whether the pressure within the tubing lumen is within a predefined range; and if it is determined that the pressure within the tubing lumen is within the predefined range, presenting a third indication to the operator to adjust the position of the catheter lumen until the pressure within the tubing lumen is less than a threshold aspiration pressure.

11. A method according to claim 7, further comprising:

after automatically establishing fluid communication between the tubing lumen and the catheter lumen, determining whether the pressure within the tubing lumen is within a predefined range; and if it is determined that the pressure within the tubing lumen is within the predefined range, automatically adjusting the position of the catheter lumen until the pressure within the tubing lumen is less than a threshold aspiration pressure.

12. A method according to claim 7, further comprising:

after automatically establishing fluid communication between the tubing lumen and the catheter lumen, determining whether the pressure within the tubing lumen is within a predefined range; and if it is determined that the pressure within the tubing lumen is within the predefined range, presenting a second indication to the operator to adjust the position of the catheter lumen until the pressure within the tubing lumen is less than a threshold aspiration pressure.

\* \* \* \* \*